US012767780B2

(12) United States Patent
Campos et al.

(10) Patent No.: US 12,767,780 B2
(45) Date of Patent: Oct. 20, 2026

(54) DEPOLYMERIZATION OF POLYURETHANES FOR CIRCULAR ECONOMY PLASTICS

(71) Applicants: International Business Machines Corporation, Armonk, NY (US); The Trustees of Columbia University in the City of New York, New York, NY (US)

(72) Inventors: Luis M. Campos, New York, NY (US); Dino Wu, New York, NY (US); James L. Hedrick, Pleasanton, CA (US); Nathaniel H. Park, San Jose, CA (US)

(73) Assignees: International Business Machines Corporation, Armonk, NY (US); The Trustees of Columbia University in the City of New York, New York, NY (US)

( * ) Notice: Subject to any disclaimer, the term of this patent is extended or adjusted under 35 U.S.C. 154(b) by 735 days.

(21) Appl. No.: 18/205,437

(22) Filed: Jun. 2, 2023

(65) Prior Publication Data

US 2024/0400786 A1 Dec. 5, 2024

(51) Int. Cl.
*C08J 11/16* (2006.01)
*C07C 1/32* (2006.01)
(Continued)

(52) U.S. Cl.
CPC ............... *C08J 11/16* (2013.01); *C07C 1/323* (2013.01); *C07C 15/08* (2013.01); *C07C 17/367* (2013.01);
(Continued)

(58) Field of Classification Search
CPC ............. C08J 11/16; C08J 11/24; C08J 11/28; C08J 2375/04; C08J 2375/08; C08J 2375/12;
(Continued)

(56) References Cited

U.S. PATENT DOCUMENTS

| | | | |
|---|---|---|---|
| 5,386,055 | A | 1/1995 | Lee |
| 7,897,651 | B2 | 3/2011 | Kazutoshi |

(Continued)

FOREIGN PATENT DOCUMENTS

| | | |
|---|---|---|
| EP | 1673180 B1 | 8/2007 |
| EP | 4137525 A1 | 2/2023 |

(Continued)

OTHER PUBLICATIONS

Gama, N. et al. Recycling of polyurethane scraps via acidolysis. Chemical Engineering Journal 395 (2020) 125102. (Year: 2020).*

*Primary Examiner* — Christina H. W. Rosebach
(74) *Attorney, Agent, or Firm* — CHIP LAW GROUP

(57) ABSTRACT

Introduce into a reactor a polyurethane having a benzylic linkage. In one aspect, induce a chemical reduction through a reducing agent and a catalyst to depolymerize the polyurethane having the benzylic linkage. In another aspect, introduce hydrogen bromide into the reactor, and react the polyurethane with the hydrogen bromide to recover constituents of the polyurethane via acid-catalyzed bromine-substitution to cleave the benzylic linkage of the polyurethane.

34 Claims, 11 Drawing Sheets

(51) Int. Cl.

| | |
|---|---|
| ***C07C 15/08*** | (2006.01) |
| ***C07C 17/367*** | (2006.01) |
| ***C07C 209/62*** | (2006.01) |
| ***C07C 211/09*** | (2006.01) |
| ***C07C 211/36*** | (2006.01) |
| ***C08G 18/22*** | (2006.01) |
| ***C08G 18/82*** | (2006.01) |
| ***C08G 85/00*** | (2006.01) |
| ***C08J 11/24*** | (2006.01) |
| *C08G 18/32* | (2006.01) |

(52) U.S. Cl.

CPC .......... *C07C 209/62* (2013.01); *C07C 211/09* (2013.01); *C07C 211/36* (2013.01); *C08G 18/222* (2013.01); *C08G 18/82* (2013.01); *C08G 85/004* (2013.01); *C08J 11/24* (2013.01); *C08G 18/3215* (2013.01); *C08J 2375/04* (2013.01); *C08J 2375/08* (2013.01); *C08J 2375/12* (2013.01); *Y02W 30/62* (2015.05)

(58) Field of Classification Search

CPC ................ C07C 17/367; C07C 209/62; C07C 211/09; C07C 211/36; C08G 18/222; C08G 18/82; C08G 18/3215; C08G 85/004; Y02W 30/62

See application file for complete search history.

(56) References Cited

U.S. PATENT DOCUMENTS

| | | | | |
|---|---|---|---|---|
| 9,095,142 | B2 | 8/2015 | Gu | |
| 10,822,469 | B2 | 11/2020 | Stubblefield | |
| 2005/0288508 | A1* | 12/2005 | Hedrick | C07C 67/03 548/101 |
| 2010/0093880 | A1 | 4/2010 | Bergfeld | |
| 2024/0117141 | A1* | 4/2024 | Mihan | C08J 11/16 |

FOREIGN PATENT DOCUMENTS

| | | | |
|---|---|---|---|
| WO | 2023275031 | A1 | 1/2023 |
| WO | 2023275036 | A1 | 1/2023 |
| WO | 2023275038 | A1 | 1/2023 |

* cited by examiner

FIG. 3

| ENTRY | POLYMER | Bis-E | Bis-Nu | REACTION TEMP. (°C) | SELECTIVITY (%) | $M_n$ (kDa) | D |
|---|---|---|---|---|---|---|---|
| 1 | PCa | bE1 | bX1a | RT | 89 | 3.6 | 1.72 |
| 2 | PCb | bE1 | bX1b | RT | 97 | 2.6 | 1.35 |
| 3 | PCc | bE1 | bX1c | RT | >99 | 3.0 | 1.28 |
| 4 | PCd | bE1 | bX2 | RT | 95 | 4.0 | 1.22 |
| 5 | PCe | bE1 | bX3 | RT | 98 | 4.1 | 1.63 |
| 6 | PUa | bE1 | bX4a | RT | >99 | 16 | 1.63 |
| 7 | PUa | bE1 | bX4a | 80 | >99 | 41 | 2.31 |
| 8 | PUb | bE2 | bX4a | RT | 78 | 14 | 1.19 |
| 9 | PUc | bE1 | bX4b | RT | >99 | 12 | 1.32 |
| 10 | PUd | bE1 | bX4c | RT | >99 | 13 | 2.21 |
| 11 | PUe | bE1 | bX5a | RT | 60 | 15 | 1.23 |
| 12 | PUe | bE1 | bX5a | 80 | 70 | 78 | 1.85 |
| 13 | PUf | bE1 | bX5b | RT | 81 | 17 | 2.31 |
| 14 | PUg | bE2 | bX5b | RT | 83 | 16 | 1.48 |
| 15 | PUh | bE3 | bX5b | RT | – | 420 | 1.32 |
| 16 | PUi | bE4 | bX5b | RT | >99 | 367 | 1.04 |
| 17 | PUj | bE1 | bX6 | RT | – | 5.1 | 1.19 |
| 18 | PUj | bE1 | bX6 | 80 | – | 4.5 | 1.46 |
| 19 | PUk | bE1 | bX7 | RT | – | 17 | 2.31 |
| 20 | PUk | bE1 | bX7 | 80 | – | 64 | 1.94 |
| 21 | PUl | bE1 | bX8 | RT | – | 4.0 | 1.25 |
| 22 | PUl | bE1 | bX8 | 80 | – | 46 | 1.11 |
| 23 | PUm | bE1 | bX9 | 80 | – | 82 | 1.30 |
| 24 | PUn | bE1 | bX10 | 80 | – | 6.9 | 1.42 |

POLYCARBONATE PCa

POLYCARBONATE PCb

POLYCARBONATE PCc

POLYCARBONATE PCd

POLYCARBONATE PCe

POLYURETHANE PUa

POLYURETHANE PUb

POLYURETHANE PUc

POLYURETHANE PUd

POLYURETHANE PUe (COPOLYMER; 3:2 POLYURETHANE/TERTIARY AMINE RATIO)

POLYURETHANE PUf

POLYURETHANE PUg

POLYURETHANE PUh

POLYURETHANE PUi

POLYURETHANE PUj

POLYURETHANE PUk

POLYURETHANE PUl

POLYURETHANE PUm

POLYURETHANE PUn

DEPOLYMERIZATION OF POLYURETHANES FOR CIRCULAR ECONOMY PLASTICS

BACKGROUND

The present invention relates generally to the chemical arts and, more particularly, to plastics and recycling thereof, and to carbon neutrality.

Environmental pollution from plastic waste is driving research into delivering new ways to treat plastic waste. While packaging waste is the most visible, plastic waste comes from a much wider range of applications, from fashion to automotive and construction to healthcare. Beyond these ecological considerations, the waste of millions of tons of plastic that currently cannot be recycled results in an estimated economic loss of between 80 and 120 billion dollars each year.

As it currently stands, there are no effective ways to revert polyurethanes to monomers that can be readily recycled.

BRIEF SUMMARY

Principles of the invention provide techniques for depolymerization of polyurethanes for circular economy plastics and the like. In one aspect, an exemplary method for depolymerizing polyurethanes includes introducing into a reactor a polyurethane having a benzylic linkage; and inducing a chemical reduction through a reducing agent and a catalyst to depolymerize the polyurethane having the benzylic linkage.

Optionally, the reducing agent comprises hydrogen.

Optionally, the chemical reduction comprises reacting the polyurethane with the hydrogen in the presence of the catalyst to recover constituents of the polyurethane via hydrogenolysis to cleave the benzylic linkage of the polyurethane.

Optionally, the catalyst comprises palladium over carbon.

The benzylic linkage advantageously allows the method to optionally be carried out at room temperature.

In another aspect, another exemplary method for depolymerizing polyurethanes includes introducing into a reactor a polyurethane having a benzylic linkage; introducing hydrogen bromide into the reactor; and reacting the polyurethane with the hydrogen bromide to recover constituents of the polyurethane via acid-catalyzed bromine-substitution to cleave the benzylic linkage of the polyurethane.

The benzylic linkage advantageously allows the method to optionally be carried out at room temperature.

As used herein, "facilitating" an action includes performing the action, making the action easier, helping to carry the action out, or causing the action to be performed. Thus, by way of example and not limitation, instructions executing on one processor might facilitate an action carried out by chemical process equipment, by sending appropriate data or commands to cause or aid the action to be performed. Where an actor facilitates an action by other than performing the action, the action is nevertheless performed by some entity or combination of entities.

Techniques as disclosed herein can provide substantial beneficial technical effects. Some embodiments may not have these potential advantages and these potential advantages are not necessarily required of all embodiments. By way of example only and without limitation, one or more embodiments may provide one or more of:

- techniques to revert polyurethane to its constituent monomers using a low energy, environmentally friendly, carbon-neutral process;
- techniques wherein $CO_2$ is released upon depolymerization in a carbon neutral matter;
- techniques wherein the recovered amine can be repolymerized into polyurethanes or upcycled into other high value materials;
- techniques wherein the recovered xylene dibromide can be repolymerized into polymers or other high value materials; and
- techniques mild depolymerization conditions mitigate any carbon offset of the transformation.

These and other features and advantages will become apparent from the following detailed description of illustrative embodiments thereof, which is to be read in connection with the accompanying drawings.

BRIEF DESCRIPTION OF THE DRAWINGS

The following drawings are presented by way of example only and without limitation, wherein like reference numerals (when used) indicate corresponding elements throughout the several views, and wherein:

FIG. 3 is a table of polymers synthesized from the bis-electrophile (bE)/bis-nucleophile (bX) combinations depicted in FIGS. 2A and 2B, according to aspects of the invention;

DETAILED DESCRIPTION

Figure 1A:
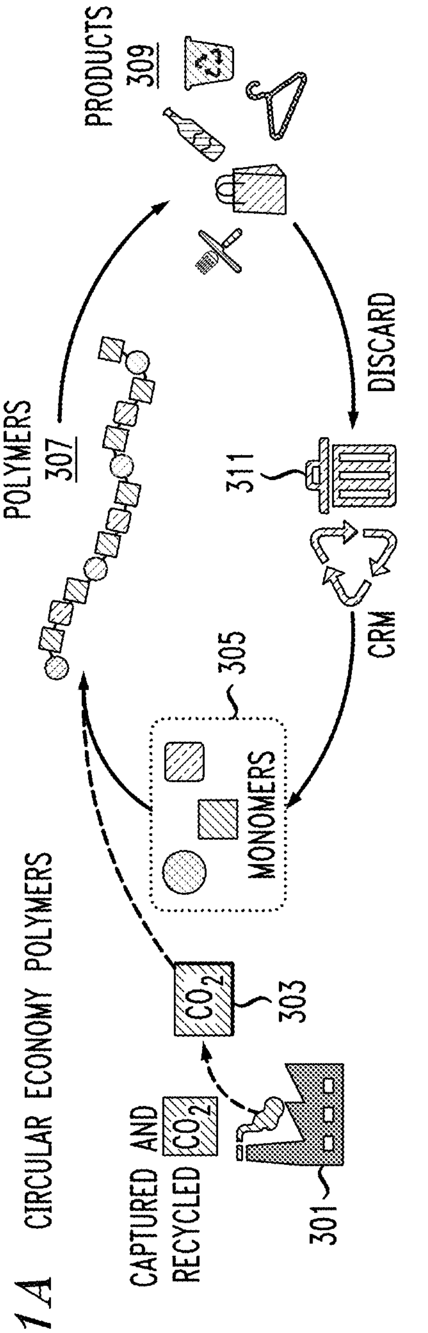
FIG. 1A shows a circular economy of plastics, according to an aspect of the invention.

Principles of inventions described herein will be in the context of illustrative embodiments. Moreover, it will become apparent to those skilled in the art given the teachings herein that numerous modifications can be made to the embodiments shown that are within the scope of the claims. That is, no limitations with respect to the embodiments shown and described herein are intended or should be inferred.

Carbon dioxide ($CO_2$) is an abundant C1 (molecule with one carbon atom) feedstock with significant potential to produce versatile building blocks in synthetic applications. Given the adverse impact of $CO_2$ on the atmosphere, it is advantageous to devise strategies for upcycling it into useful materials, such as plastics. In order to activate such a stable molecule, superbases offer viable modes of binding to $CO_2$. We have found that a superbase cyclopropenimine derivative exhibits exceptional proficiency in activating $CO_2$ and mediating its polymerization at ambient temperature and pressure. Significantly, we have found that resulting polymers can be chemically recycled to monomers, thereby enabling a significant step toward establishing a circular economy for plastics. Furthermore, the versatility of this reaction can be extended to monofunctional amines and alcohols, yielding a variety of functional carbonates and carbamates.

The significant gains from modern polymer design principles over the last century, based on both chemical innovation and economically efficient mass manufacturing, have driven economies worldwide by making soft matter ubiquitous in everyday life. However, the practice of single-use and disposal of these durable materials is unsustainable, leading to unintended environmental consequences. Addressing the significant amounts of plastic waste by moving towards a circular materials economy has become a pertinent challenge in polymer chemistry. New strategies and transformations are now emerging to develop polymers that can undergo chemical recycling to monomers (CRM), maintaining a closed-loop life cycle. Such approaches involve the intricate design of monomers for their ability to undergo polymerization and depolymerization. In the realm of commodity plastics, catalytic depolymerization of poly(ethylene terephthalate) (PET) to monomer has been demonstrated, as well as its upcycling (typically by aminolysis) to materials ranging from engineering thermoplastics to therapeutics. Emerging alternatives such as bioplastics synthesized from biomass-derived monomers and recyclable networks also offer new avenues of exploration. Recent advances in metal catalysis have led to the synthesis of carbon monoxide (CO)-containing polyethylene, which can more readily undergo photodegradation. Developing strategies to incorporate carbon dioxide ($CO_2$) in the synthesis of polymers offers transformative advantages in upcycling and to maintain carbon neutrality.

Despite the potential utility of $CO_2$ as a low cost and abundant C1 synthon, only a handful of processes use it in the synthesis of fine chemicals or materials. Noteworthy independent examples include the organometallic catalyzed direct polymerization of $CO_2$ with various epoxides, yielding polymers from a pallet of monomers. While numerous reports detail the use of reagents and catalysts to activate $CO_2$ and convert it into cyclic monomers, its limited mode of reactivity has dwarfed the development of modular transformations for its upcycling and/or recycling within synthetic polymers. In many cases, such reactions exhibit limited substrate scope and forcing conditions, such as high temperature and pressure. Many of the obstacles surrounding the direct polymerization of $CO_2$ can be attributed to its thermodynamic stability and gaseous physical state at room temperature. Organic compounds commonly used for $CO_2$ transformations—such as amidines, guanidines, phosphazenes, and organoboranes—are challenging to synthetically modify, prohibiting systematic functional modifications to tune their reactivity. In comparison, organometallic systems suffer from high catalyst loadings or additional additives, while certain anionic compounds require harsh, strongly basic conditions. Therefore, a significant challenge is to develop efficient reagents that enable user-friendly transformations under mild conditions to consume and/or recycle $CO_2$-creating the foundation of a circular carbon economy. Disclosed herein is an organic superbase that incorporates $CO_2$ as a building block for carbonation polymerizations. Also disclosed are techniques that allow polyurethanes (PUs) to be designed to undergo CRM, maintaining a closed-loop cycle.

We have previously filed one or more patent applications that disclosed the synthesis of a single family of cyclopropylamine (CPI)-based molecules and polymers that can be exploited in upcycling of $CO_2$. Specifically, we were able to upcycle CPI-captured $CO_2$ to generate polyurethanes from amines and selected electrophiles. In this way, we can make one of the most pervasively used polymers without the use of toxic isocyanates, giving rise to a broad range of glass temperatures (Tg) and mechanical properties. As it currently stands, there are no effective ways to revert polyurethanes to monomers that can be readily recycled. To this end, we have discovered a way to revert polyurethane to its constituent monomers using a low energy process. We found that the polyurethane prepared from $CO_2$ was readily recyclable by catalytic hydrogenolysis (Pd/carbon) or acid-catalyzed bromide-substitution (HBr/HOAc) to allow the recovery of the amine used in the synthesis.

Figure 1B:
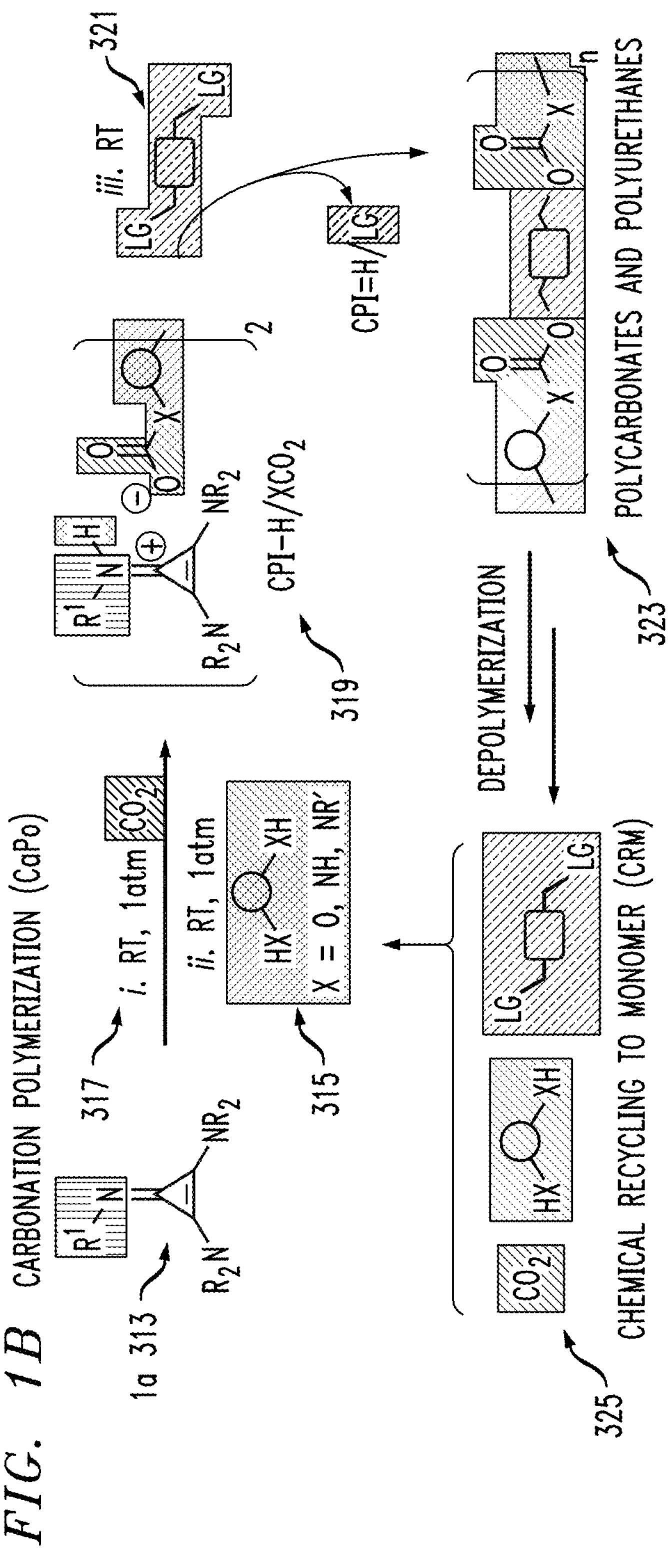
FIG. 1B shows cyclic carbonation polymerization and depolymerization, according to an aspect of the invention.

FIGS. 1A and 1B depict an exemplary strategy to develop $CO_2$-based circular economy polymers (CEPs). Throughout the figures, standard organic chemistry skeletal formulas, familiar to the skilled artisan, are employed. Specifically, unless stated or illustrated otherwise:

- single, double, and triple bonds are depicted as single, double, and triple line segments;
- an unlabeled vertex is understood to represent a carbon attached to the number of hydrogens required to satisfy the octet rule;
- a vertex labeled with a formal charge and/or nonbonding electron(s) is understood to have the number of hydrogen atoms required to give the carbon atom these indicated properties;
- carbon and hydrogen atoms are generally not explicitly drawn, while skeletal atoms other than carbon or hydrogen (i.e., heteroatoms) are drawn explicitly;
- Me refers to a methyl group;
- Et refers to an ethyl group;
- Bn refers to a benzyl group; and
- n-Bu refers to a normal butyl group.

FIG. 1A represents an exemplary circular economy of plastics, enabled by aspects of the invention, where $CO_2$-based polymers are synthesized, used in plastic products, and chemically recycled to monomers (CRM) for subsequent polymerizations. In particular, $CO_2$ 303 is captured from an industrial process at 301 and used together with monomers 305 to synthesize polymers 307 used to make products 309. The products are recycled at 311 to obtain the CRM 305. FIG. 1B depicts the cyclic carbonation polymerization (CaPo) process for the synthesis of CEPs at room temperature (RT). Bis-nucleophiles (bX) 313 are reacted in the presence of a CPI (see discussion of CPIs below) derivative 315 and $CO_2$, as shown at 317, to produce bis-carbamate intermediates 319, subsequently reacting with bis-electrophiles (bE) 321 to make polycarbonates and polyurethanes 323 designed for CRM 325.

Considering that superbases can react with $CO_2$, cyclopropenimines (CPIs) developed for Brønsted base catalysis are attractive candidates for Lewis base activation of $CO_2$. The CPIs were cleverly designed with a driving force that forms a stable, 2π-electron Hückel aromatic conjugate acid (CPI-H), leading to a higher $pK_a$ than analogous bases. Their modular synthesis from inexpensive, commercially available starting materials allows for systematic incorporation of a variety of functional groups with unique steric and electronic properties to investigate reactivity trends. Over the last decade, CPIs have been employed in a variety of organocatalytic transformations, such as lactide polymerizations, Mannich and Michael reactions. We have found that a superbase cyclopropenimine derivative, 1a (labeled 313 in the figures), can readily react with $CO_2$ at atmospheric pressure, effectively mediating $CO_2$ transfer for room temperature carbonation polymerizations (CaPo) and other functional transformations (See FIG. 1B). It is believed that the superbase can transfer $CO_2$ onto readily available alcohols and amines to form polymers and small molecules with carbonate or carbamate linkages. We note that CPIs offer modularity to vary the R and $R^1$ groups (as shown in view 313 in FIG. 1B) in order to alter their properties and reactivity, but a non-limiting example focuses on one particular derivative of the superbase, 1a, for the synthesis of CEPs under mild conditions. One or more embodiments provide both a modular framework for $CO_2$ utilization in polymerizations, as well as the potential to exploit other functional CPIs in essential carbon transformation technologies. The R and $R^1$ groups can be any appropriate substituent as will be apparent to persons of ordinary skill given the teachings herein.

Carbonation Polymerization

Unlike synthetic methods that require high temperatures (>100° C.), high pressures (>1 atm), and extended reaction times, the CPI-mediated carbonation polymerization (CaPo) proceeds at room temperature (RT) and ambient pressure. The reaction was tested by first bubbling $CO_2$ in the presence of 1a, followed by addition of a bis-nucleophile, bX (referring generally to bX1a through bX10 in FIGS. 2A and 3), to enable the formation of intermediate 2 (labeled 319 in FIG. 1B); and subsequently adding a bis-electrophile, bE (referring generally to bE1 through bE4 in FIGS. 2B and 3), as shown in FIG. 1B. These first two steps lead to a pseudo molar equivalency between the carbonate/carbamate, $$XCO_2^-,$$

Figure 2A:
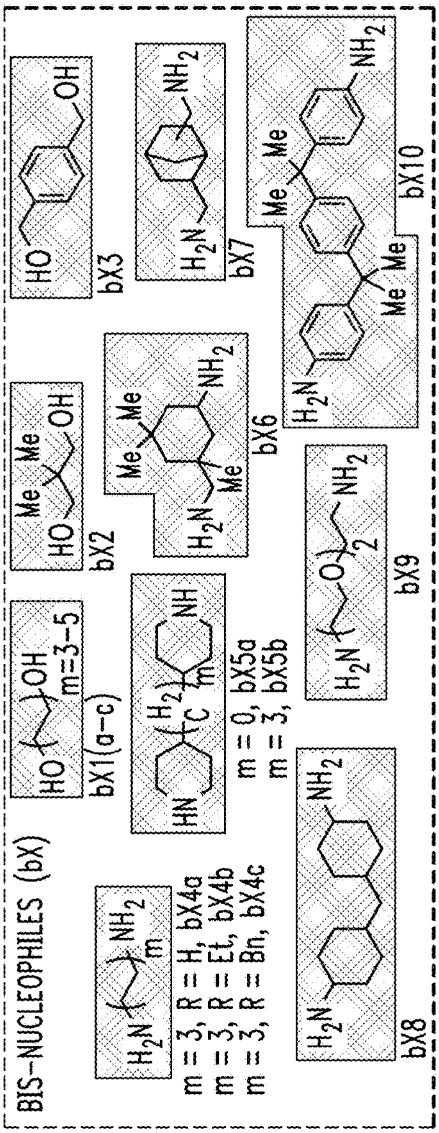
FIG. 2A shows bis-nucleophiles (bX) used for the synthesis of polycarbonates and polyurethanes, according to an aspect of the invention.
Figure 2B:
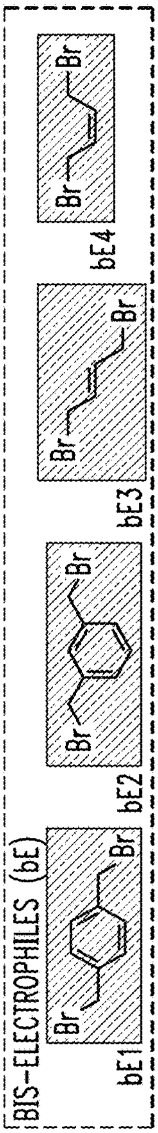
FIG. 2B shows bis-electrophiles used for the synthesis of polycarbonates and polyurethanes, according to an aspect of the invention.

(X=O, NH, NR' see 315) and the bEs, minimizing the direct reaction between bX and bE. The variety of electrophiles and nucleophiles is shown in FIGS. 2A and 2B, and the resulting polymers are listed in the table of FIG. 3. Note that "bX1" refers to any of bX1a, bX1b, and bX1c; "bX4" refers to any of bX4a, bX4b, and bX4c; and "bX5" refers to any of bX5a and bX5b. As proof-of-principle, the selection of bX was varied between amines and alcohols and focused on primary benzylic and allylic halides as the electrophiles. In general, when alkanediols bX1-bX3 were used as nucleophiles to synthesize polycarbonates, the reaction led to products with relatively low molecular mass, even after heating to 45° C. ($M_n$~3-4 kDa, polymers PCa-e, Table of FIG. 3). The carbonation polymerization of bis-alcohols was found to be sluggish due to the incomplete conversion to corresponding carbonates. For example, using bX1a, only 50% of the carbonate 2a is formed, whereas the bis-amine bX8 quantitatively yields a stable bis-carbamate 2b (see FIGS. 2C and D). From the carbamate formation, the room temperature reaction using nucleophiles bX4-bX9 readily afforded polyurethanes PUa-n with a wide distribution of $M_n$, up to 410 kDa (Table of FIG. 3). Notably, the carbonation polymerization of the bis-amine bX9 exhibited low reactivity at low temperature, but heating to 80° C. yielded high Mn (82 kDa). Bis-arylamine bX10 also exhibited limited reactivity at room temperature, and heating to 80° C. also yielded a relatively low Mn polyurethane (6.9 kDa; Table of FIG. 3, entry 24). Considering the lack of diversity in the synthesis of PUs directly from $CO_2$, these findings open new avenues of exploration of PUs from readily available building blocks that advantageously overcome the need to prepare isocyanates with phosgene.

Figure 2C:
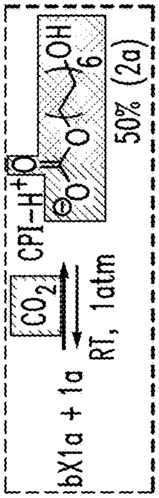
FIGS. 2C and 2D respectively show reactions of diol bX1a and diamine bX9 with nBuCPI 1a and $CO_2$, according to aspects of the invention.
Figure 2D:
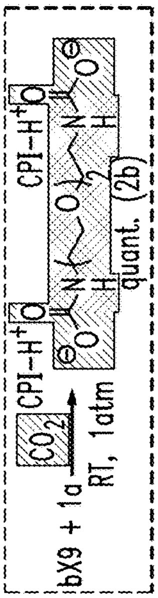
Figure 2E:
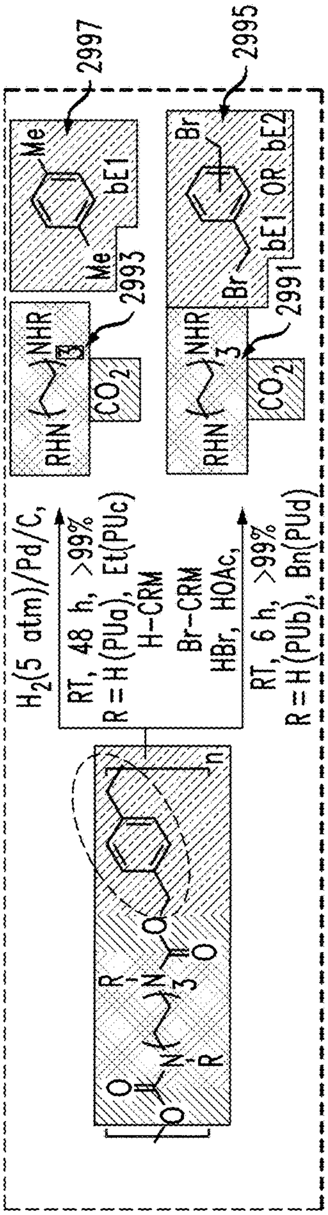
FIG. 2E shows hydrogenation-based (H-CRM) and hydrogen bromide-based (Br-CRM) chemical recycling to a monomer, according to aspects of the invention.

Considering FIGS. 2A-2E, generally depicting aspects of carbonation polymerization and depolymerization, note in FIG. 2A Bis-nucleophiles (bX) and in FIG. 2B Bis-electrophiles (bE) used for the synthesis of polycarbonates and polyurethanes. FIGS. 2C and 2D respectively show reactions of diol bX1a and diamine bX9 with nBuCPI 1a and $CO_2$; they exhibit stark differences, where the diol only reaches 50% conversion and 2b is formed quantitatively. FIG. 2E depicts chemical recycling to monomers of selected polyurethanes: Hydrogenation-based (H-CRM) (top of FIG. 2E) and Hydrogen bromide-based (Br-CRM) (bottom of FIG. 2E) chemical recycling to monomer.

The RT carbonation polymerization using readily available monomers afforded polymers with varying degrees of polymerization (Table of FIG. 3). Increasing the temperature of the reaction to 80° C. yielded polymers with significantly higher Mn, albeit the precipitated polymers were highly insoluble and showed yellow discoloration, which is indicative of direct linkage of the nucleophile with the electrophile. In general, we have found that the solubility of intermediate 2 and the growing polymer (see FIG. 1B) is significant to promote polymerization, both of which are influenced by solvent choice and counterion identity. Using 1,8-diazabicyclo[5.4.0]undec-7-ene (DBU) or triazabicyclodecene (TBD), it was also possible to form the analogous bis-carbamate anion from the amine, but in contrast to 2, these salts become insoluble upon reaction with $CO_2$, prohibiting polymerization. In examples using bX5, higher molecular weight polymers were produced, presumably due to the nucleophilicity of the piperidine moieties (entries 9-13, Table of FIG. 3). However, the high reactivity also partially promoted the direct alkylation of the amine nucleophiles, forming up to 50% of the polymer linkages. This undesired reactivity was suppressed by adding a non-polar solvent (toluene or $CH_2Cl_2$) to improve the solubility of the bis-carbamate 2, resulting in higher selectivity for urethane linkages (entries 11-14, Table of FIG. 3).

Generally, the table of FIG. 3 presents a list of polymers synthesized from the bis-electrophile (bE)/bis-nucleophile (bX) combinations depicted in FIGS. 2A and 2B. Selectivity indicates the percent conversion of bond linkages resulting in carbonate/urethane bonds. Average molecular weight ($M_n$) and dispersity (Đ) are provided, and all polymerizations were performed at 1 atm $CO_2$. The structure of each polymer is presented elsewhere herein.

A pertinent aspect of the CPI-mediated CaPo is the enabling of the synthesis of N-alkylated polyurethanes from secondary amines, as opposed to the conventional synthesis using diols and diisocyanates that only lead to NH-urethanes. Removing the urethane inter-chain hydrogen bonds provides an essential handle to readily alter the properties of the resulting polyurethanes. It was found that N-alkylated PUs exhibit drastically different glass transition temperatures ($T_g$) due to the lack of the H-bonding interaction present in NH-polyurethanes (NH-PUS) (e.g. $T_g$(PUa)=53° C. and $T_g$(PUc)=−2° C. However, additional physical and mechanical characteristics of these new plastics were observed. The N-benzylated polyurethane PUd featured a Young's modulus of 2 MPa, with no observed break at elongation>13,000%. In contrast, NH-polyurethane PUa was brittle, with only 1-2% elongation at break and a Young's modulus of 19 MPa. In the case of bis-piperidine based polyurethanes, two electrophiles with subtle structural differences were compared, bE1 and bE2, yielding polymers with drastically different Young's modulus (PUf=185 MPa and PUg=354 MPa. An advantage of the polymerizations is the ease of recovery of the CPI salt (CPI-H·Br) after trituration of the polymer. Collection of CPI-H·Br salts allowed regeneration of 1a after conventional workup techniques (14 polymerizations were carried out in serial using the same 29 g batch of 1a. Direct regeneration of 1a from the crude (untreated mixture after the reaction) is also possible by precipitating it in a biphasic system of toluene/hexane (1:1) and 1 M $Na_2CO_3$ (aq). As the polymer partitions between the aqueous and organic phases, the CPI-H·Br salt is deprotonated and is recovered from the organic phase directly, albeit this method cannot be used for base-labile polycarbonates or polyurethanes (e.g. PUc, PUd).

Considering the importance and paucity of CEPs, the potential for these polymers to be chemically recycled to monomer was tested (refer to FIG. 2E). Aliphatic polycarbonates can be hydrolyzed or trans esterified in the presence of a base. However, polyurethanes require harsh conditions involving temperatures above 150° C., which can be inefficient and prone to side reactions. From selected polymers listed in the Table of FIG. 3, the depolymerization can be achieved by hydrogenolysis (H-CRM) to cleave the benzylic C—O bond of the polyurethane. In previous studies, the hydrogenolysis depolymerization of polyurethanes has been reported to proceed at high temperature (>130° C.) and pressure (>40 bar). In an exemplary embodiment, treatment of PUc with $H_2$ (1 atm) and 5% Pd/C for 48 hours resulted in 90% conversion to monomer. Increasing the pressure to 5 atm, complete depolymerization was achieved with primary/secondary amine-based polyurethanes PUa and PUc, to produce corresponding bis-amines (bX4a and bX4b), $CO_2$ and p-xylene (see FIGS. 6A and 6B). Hydrogenolysis of the more sterically hindered PUf yielded a 90% conversion under the same conditions (see FIG. 6C). Although the recovered p-xylene is evaporated due to its volatility, distillation and conversion to the bis-electrophile via radical halogenation would close the CEP cycle. Alternatively, a more efficient reaction can be used for the depolymerizations of the labile benzylic bonds by an acid-catalyzed bromine-substitution (Br-CRM). Polymers PUb, PUd, and PUf were depolymerized with a mixture of HBr and acetic acid at RT for 6 hours, yielding the corresponding protonated diamines and dibromoxylenes (bE1 and bE2, see FIGS. 7A-7C). The recovery of the electrophiles used in the CaPo brings the process to a full circular economy.

Preparation of nBuCPI on a Multi-Gram Scale nBuCPI (1a) was prepared according to a modified procedure from Stukenbroeker, T. S., Bandar, J. S., Zhang, X., Lambert, T. H. & Waymouth, R. M. Cyclopropenimine Superbases: Competitive Initiation Processes in Lactide Polymerization. *ACS Macro Lett.* 4, 853-856 (2015). In a round-bottom flask, 1-chloro-2,3-bis(dicyclohexylamino) cycloprop-2-en-1-ylium chloride (30.0 g, 64.1 mmol, 1.00 equiv) was dissolved in $CH_2Cl_2$ (250 mL) and cooled to 0° C. in an ice bath. Then N,N-diisopropylethylamine (16.6 g, 22.3 mL, 128 mmol, 2.00 equiv) and n-butylamine (5.16 g, 6.98 mL, 70.6 mmol, 1.10 equiv) were added and the reaction was allowed to warm up to room temperature. After 18 h, the solution was washed with 1 M HCl (3×50 mL) and 1 M NaOH (3×50 mL), dried over $Na_2SO_4$, filtered and concentrated. The residue was precipitated in acetonitrile, the solid was filtered and washed with cold acetonitrile to give nBuCPI as a white solid (27.9 g, 59.7 mmol, 93.0%).

Preparation of Polycarbonates and Polyurethanes nBuCPI (1a) (2.00 eq) was suspended in acetonitrile (0.50 M) and $CO_2$ was bubbled from a balloon through a needle. When the cyclopropenimine-$CO_2$ complex was fully dissolved (from 5-20 min), the diamine (1.00 equiv) was directly added and stirred for 10 min. p-xylenedibromide (1.00 eq) was added. After stirring for at least 24 h (detailed discussion below), the solution was added to MeOH or $CH_3CN$ to precipitate the polymer. Rinsing with the same solvent afforded the polymers.

Figure 4A:
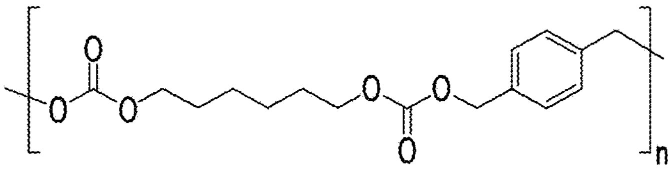
FIGS. 4A-4E show the chemical structures of polycarbonates PCa-PCe of the table of FIG. 3, according to aspects of the invention.

Referring to FIG. 4A, polycarbonate PCa was prepared according to general procedure using nBuCPI 1a (500 mg, 1.07 mmol, 2.00 equiv), 1,6-hexanediol bX1a (63.1 mg, 0.534 mmol, 1.00 equiv) and p-xylene dibromide bE1 (141 mg, 0.534 mmol, 1.00 equiv) with 72 h reaction time at RT. Precipitation and rinsing in methanol afforded PCa as a white powder (112 mg, 68%). $^1$H NMR (500 MHz, $CDCl_3$) δ 7.47-7.42 (m, 4H), 5.14 (s, 4H), 4.13 (t, J=6.6 Hz, 4H), 1.74-1.60 (m, 4H), 1.46-1.32 (m, 4H) ppm; $T_{dec}$=161° C.; $T_g$=−5.2° C.; $T_m$=85.3° C.; $M_n$=2.63 kDa, Đ=1.35; IR (ATR) 2941, 1739, 1451, 1372, 1239, 1067, 942 $cm^{-1}$.

Figure 4B:
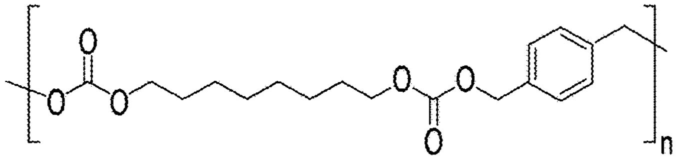

Referring to FIG. 4B, polycarbonate PCb was prepared according to general procedure using nBuCPI 1a (500 mg, 1.07 mmol, 2.00 equiv), 1,8-octanediol bX1b (78.1 mg, 0.534 mmol, 1.00 equiv) and p-xylene dibromide bE1 (141 mg, 0.534 mmol, 1.00 equiv) with 72 h reaction time at RT. Precipitation in methanol afforded PCb as a white powder (126 mg, 70%). $^1$H NMR (500 MHz, $CDCl_3$) δ 7.47-7.42 (m, 4H), 5.14 (s, 4H), 4.13 (t, J=6.6 Hz, 4H), 1.74-1.60 (m, 4H), 1.46-1.32 (m, 4H) ppm; $T_{dec}$=157° C.; $T_g$=−21.4° C.; $T_m$=67.6° C.; $M_n$=3.89 kDa, Đ=1.28; IR (ATR) 2929, 1739, 1453, 1369, 1237, 1058 $cm^{-1}$.

Figure 4C:
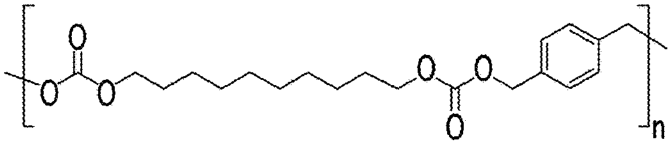

Referring to FIG. 4C, polycarbonate PCc was prepared according to general procedure using nBuCPI 1a (500 mg, 1.07 mmol, 2.00 equiv), 1,10-decanediol bX1c (93.1 mg, 0.534 mmol, 1.00 equiv) and p-xylene dibromide bE1 (141 mg, 0.534 mmol, 1.00 equiv) with 48 h reaction time at RT. Precipitation in methanol afforded PCc as a white powder (140 mg, 72%). $^1$H NMR (500 MHz, $CDCl_3$) δ 7.47-7.32 (m, 4H), 5.14 (s, 4H), 4.13 (t, J=6.6 Hz, 4H), 1.74-1.60 (m, 4H), 1.40-1.20 (m, 12H) ppm; $T_{dec}$=156° C.; $T_g$=−10.1° C.; $T_m$=75.2° C.; $M_n$=4.13 kDa, Đ=1.63; IR (ATR) 2925, 1743, 1451, 1370, 1242, 1037 $cm^{-1}$.

Figure 4D:
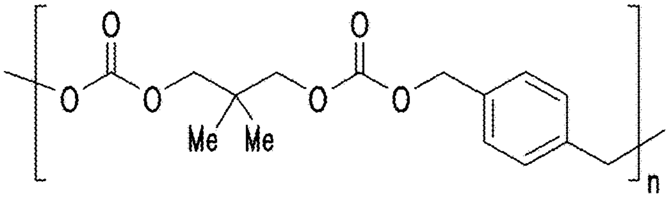

Referring to FIG. 4D, polycarbonate PCd was prepared according to general procedure using nBuCPI 1a (2.00 g, 4.28 mmol, 2.00 equiv), 2,2-dimethyl-1,3-propanediol bX2 (223 mg, 2.14 mmol, 1.00 equiv) and p-xylene dibromide bE1 (564 mg, 2.14 mmol, 1.00 equiv) with 60 h reaction time at RT. Precipitation in methanol afforded PCd as a white wax (407 mg, 65%). $^1$H NMR (500 MHz, $CDCl_3$) δ

7.40 (s, 4H), 5.16 (s, 4H), 3.99 (s, 4H), 1.00 (s, 6H) ppm; $T_{dec}$=157° C.; $T_g$=1.8° C.; $M_n$=4.02 kDa, Đ=1.22; IR (ATR) 2961, 1739, 1454, 1384, 1227, 953 $cm^{-1}$.

Figure 4E:
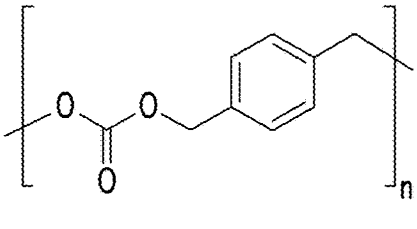

Referring to FIG. 4E, polycarbonate PCe was prepared according to general procedure using nBuCPI 1a (500 mg, 1.07 mmol, 2.00 equiv), 1,4-benzenedimethanol bX3 (73.8 mg, 0.534 mmol, 1.00 equiv) and p-xylene dibromide bE1 (141 mg, 0.534 mmol, 1.00 equiv) with 48 h reaction time at RT. Precipitation in methanol afforded PCe as a white powder (121 mg, 69%). $^1$H NMR (500 MHz, $CDCl_3$) δ 7.47-7.32 (m, 4H), 5.18 (s, 4H) ppm; $T_{dec}$=164° C.; $M_n$=3.55 kDa, Đ=1.72; IR (ATR) 2963, 1739, 1446, 1383, 1227, 930 $cm^{-1}$.

Figure 5A:
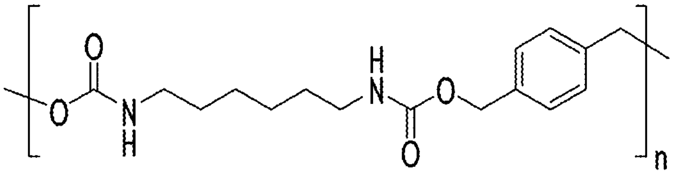
FIGS. 5A-5N show the chemical structures of polyurethanes PUa-PUn of the table of FIG. 3, according to aspects of the invention.

Referring to FIG. 5A, polyurethane PUa was prepared according to general procedure using nBuCPI 1a (4.00 g, 8.56 mmol, 2.00 equiv), 1,6-diaminohexane bX4a (497 mg, 4.28 mmol, 1.00 equiv) and p-xylene dibromide bE1 (1.13 g, 4.28 mmol, 1.00 equiv) with 24 h reaction time at RT. Precipitation in MeOH afforded PUa as a white powder (980 mg, 75%). $^1$H NMR (400 MHz, $CDCl_3$) δ 7.47-7.29 (m, 4H), 5.09 (br s, 4H), 3.19 (br s, 4H), 1.42-1.27 (m, 8H) ppm; $T_{dec}$=256° C.; $T_g$=52.9° C.; $M_n$=16.0 kDa, Đ=1.63; IR (ATR) 3344, 2924, 1701, 1509, 1248, 1018 $cm^{-1}$.

Figure 5B:
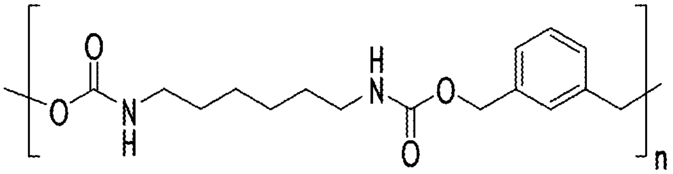

Referring to FIG. 5B, polyurethane PUb was prepared according to general procedure using nBuCPI 1a (4.00 g, 8.56 mmol, 2.00 equiv), 1,6-hexanediamine bX4a (497 mg, 4.28 mmol, 1.00 equiv) and m-xylene dibromide bE2 (1.13 g, 4.28 mmol, 1.00 equiv) with 24 h reaction time at RT. Precipitation in MeOH afforded PUb as a white powder (932 mg, 71%). $^1$H NMR (400 MHz, $CDCl_3$) δ 7.47-7.29 (m, 4H), 5.06 (br s, 4H), 3.14 (br s, 4H), 1.61-1.122 (m, 8H) ppm; $T_{dec}$=257° C.; $T_g$=24.4° C.; $M_n$=14.4 kDa, Đ=1.19; IR (ATR) 3318, 2929, 1685, 1530, 1252, 1132 $cm^{-1}$.

Figure 5C:
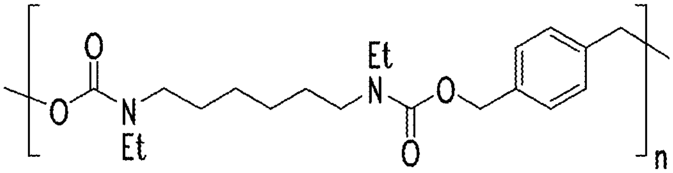

Referring to FIG. 5C, polyurethane PUc was prepared according to general procedure using nBuCPI 1a (2.00 g, 4.28 mmol, 2.00 equiv), N,N-diethyl-1,6-hexyldiamine bX4b (368 mg, 2.14 mmol, 1.00 equiv) and p-xylene dibromide bE1 (564 mg, 2.14 mmol, 1.00 equiv) with 24 h reaction time at RT. Precipitation in acetonitrile afforded PUc as a transparent sticky wax (462 mg, 60%). $^1$H NMR (500 MHz, $CDCl_3$) δ 7.33 (s, 4H), 5.11 (s, 4H), 3.28 (br s, 4H), 3.21 (br s, 4H), 1.60-1.46 (m, 4H), 1.36-1.20 (m, 4H), 1.17-1.01 (m, 6H) ppm; $T_{dec}$=257° C.; $T_g$=−2.7° C.; $M_n$=12.2 kDa, Đ=1.32; IR (ATR) 2930, 1693, 1460, 1400, 1294, 1181, 1020 $cm^{-1}$.

Figure 5D:
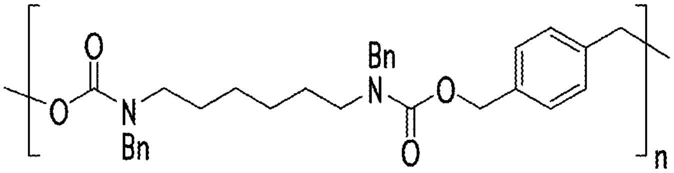

Referring to FIG. 5D, polyurethane PUd was prepared according to general procedure using nBuCPI 1a (4.00 g, 8.56 mmol, 2.00 equiv), N,N-dibenzyl-1,6-hexyldiamine bX4c (1.27 g, 4.28 mmol, 1.00 equiv) and p-xylene dibromide bE1 (1.13 mg, 0.534 mmol, 1.00 equiv) with 24 h reaction time at RT. Precipitation in acetonitrile afforded PUd as a yellowish sticky glue-like solid (1.36 g, 65%). $^1$H NMR (500 MHz, $CDCl_3$) δ 7.34-7.17 (m, 12H), 7.17-7.09 (m, 2H), 5.13 (br s, 4H), 4.45 (br s, 4H), 3.29-3.05 (m, 4H), 1.50-1.34 (m, 4H), 1.23-1.06 (m, 4H) ppm; $T_{dec}$=260° C.; $T_g$=10.5° C.; $M_n$=13.4 kDa, Đ=2.21; IR (ATR) 2931, 1690, 1496, 1453, 1416, 1219, 1072 $cm^{-1}$.

Figure 5E:
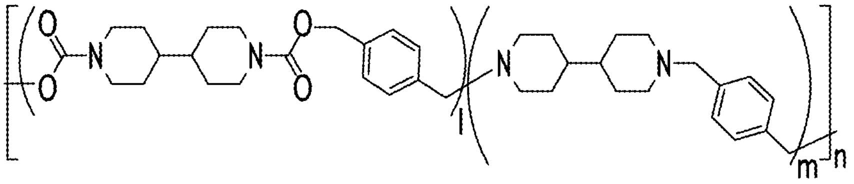

Referring to FIG. 5E, polyurethane PUe was prepared according to general procedure using nBuCPI 1a (1.00 g, 2.14 mmol, 2.00 equiv), 4,4'-bipiperidine bX5a (180 mg, 1.07 mmol, 1.00 equiv) and p-xylene dibromide bE1 (282 mg, 1.07 mmol, 1.00 equiv) with 24 h reaction time at RT with slight modifications. Acetonitrile/$CH_2Cl_2$ (4:1, 5.0 mL) was used as solvent instead of only $CH_3CN$ to increase solubility. Precipitation in acetonitrile (150 mL) and rinsing with acetonitrile (20 mL) afforded PUe as a white powder (332 mg, 87%). $^1$H NMR (500 MHz, $CDCl_3$) δ 7.34 (s, 1.68H), 7.29 (s, 2.32H) 5.10 (br s, 2.32H), 4.20 (br s, 2.32H), 3.48 (br s, 1.68H) 2.92 (br s, 1.68H), 2.71 (br s, 2.32H), 1.91 (br s, 1.68H), 1.74-1.00 (m, 10H) ppm; $T_{dec}$=250° C.; $T_g$=97.0° C.; $M_n$=15.1 kDa, Đ=1.23; IR (ATR) 2933, 1694, 1432, 1227, 1015 $cm^{-1}$.

Figure 5F:
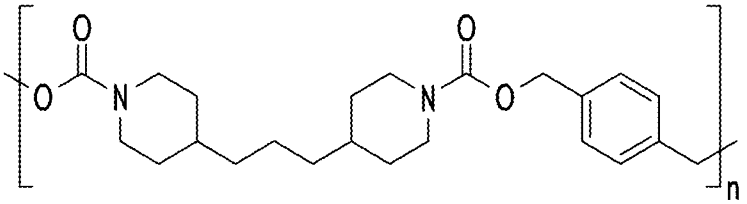

Referring to FIG. 5F, polyurethane PUf was prepared according to general procedure using nBuCPI 1a (4.00 g, 8.56 mmol, 2.00 equiv), 1,3-bis(4-piperidinyl)propane bX5b (899 mg, 4.28 mmol, 1.00 equiv) and p-xylene dibromide bE1 (1.13 mg, 4.28 mmol, 1.00 equiv) with 24 h reaction time at RT with slight modifications. Toluene/$CH_3CN$ (1:15, 16 mL) was used as solvent instead of only $CH_3CN$ to increase solubility. Precipitation in acetonitrile (250 mL) and rinsing with acetonitrile (50 mL) afforded PUf as a white solid (1.64 g, 96%). $^1$H NMR (500 MHz, $CDCl_3$) δ 0.44-7.29 (m, 4H), 5.10 (s, 3H), 4.14 (s, 3H), 3.56-3.40 (m, 1H), 3.56-2.50 (m, 4H), 1.90 (br s, 1H), 1.75-1.00 (m, 16H) ppm; $T_{dec}$=266° C.; $T_g$=52.2° C.; $M_n$=17.0 kDa, Đ=2.31; IR (ATR) 2918, 1693, 1432, 1361, 1218, 1078 $cm^{-1}$.

Figure 5G:
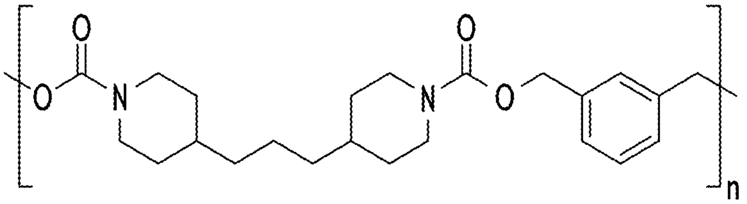

Referring to FIG. 5G, Polyurethane PUg was prepared according to general procedure using nBuCPI 1a (4.00 g, 8.56 mmol, 2.00 equiv), 1,3-bis(4-piperidinyl)propane bX5b (899 mg, 4.28 mmol, 1.00 equiv) and m-xylene dibromide bE2 (1.13 mg, 4.28 mmol, 1.00 equiv) with 24 h reaction time at RT with slight modifications. Toluene/$CH_3CN$ (1:15, 16 mL) was used as solvent instead of only $CH_3CN$ to increase solubility. Precipitation in acetonitrile (250 mL) and rinsing with acetonitrile (50 mL) afforded PUg as a white solid (1.58 g, 92%). $^1$H NMR (500 MHz, $CDCl_3$) δ 7.44-7.29 (m, 4H), 5.11 (s, 3.4H), 4.15 (s, 3.4H), 3.60-3.24 (m, 0.6H), 3.05-2.48 (m, 4H), 1.93 (br s, 0.6H), 1.80-1.00 (m, 16H) ppm; $T_{dec}$=253° C.; $T_g$=54.4° C.; $M_n$=16.0 kDa, Đ=1.48; IR (ATR) 2922, 1694, 1427, 1361, 1219, 1080 $cm^{-1}$.

Figure 5H:
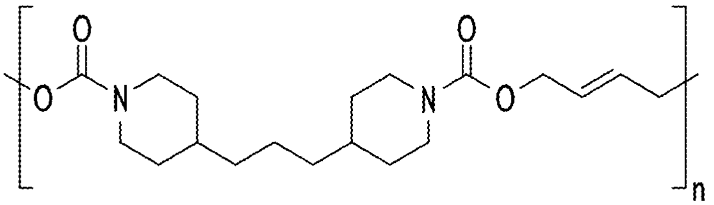

Referring to FIG. 5H, polyurethane PUh was prepared according to general procedure using nBuCPI 1a (4.00 g, 8.56 mmol, 2.00 equiv), 1,3-bis(4-piperidinyl)propane bX5b (899 mg, 4.28 mmol, 1.00 equiv) and trans-1,4-dibromobut-2-ene bE3 (915 mg, 4.28 mmol, 1.00 equiv) with 24 h reaction time at RT with slight modifications. Toluene/$CH_3CN$ (1:15, 16 mL) was used as solvent instead of only $CH_3CN$ to increase solubility. Precipitation in MeOH (250 mL) and rinsing with MeOH (50 mL) afforded PUh as a white solid (1.34 g, 89%). $^1$H NMR (500 MHz, $CDCl_3$) δ 6.04-5.63 (m, 2H), 4.59 (br s, 4H), 4.11 (br s, 4H), 2.74 (br s, 4H), 1.66 (br s, 4H), 1.45-1.00 (m, 12H) ppm; $T_{dec}$=244° C.; $T_g$=52.9° C.; $M_n$=420.0 kDa, Đ=1.32; IR (ATR) 2918, 1692, 1429, 1366, 1220, 1102 $cm^{-1}$.

Figure 5I:
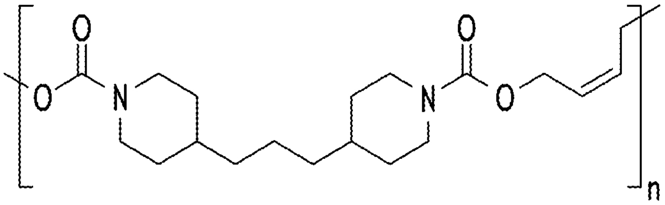

Referring to FIG. 5I, polyurethane PUi was prepared according to general procedure using nBuCPI 1a (4.00 mg, 8.56 mmol, 2.00 equiv), 1,3-bis(4-piperidinyl)propane bX5b (899 mg, 4.28 mmol, 1.00 equiv) and cis-1,4-dibromobut-2-ene bE4 (915 mg, 4.28 mmol, 1.00 equiv) with 24 h reaction time at RT with slight modifications. Toluene/$CH_3CN$ (1:15, 16 mL) was used as solvent instead of only $CH_3CN$ to increase solubility. Precipitation in MeOH (250 mL) and rinsing with MeOH (50 mL) afforded PUi as a sticky white glue-like solid (1.12 g, 75%). $^1$H NMR (500 MHz, $CDCl_3$) δ 5.76 (t, J=4.0 Hz, 2H), 4.70 (d, J=4.0 Hz, 4H), 4.25-3.99 (m, 4H), 2.75 (br s, 4H), 1.79-1.54 (m, 4H), 1.46-1.09 (m, 12H) ppm; $T_{dec}$=244° C.; $T_g$=54.4° C.; $M_n$=367 kDa, Đ=1.04; IR (ATR) 2919, 1691, 1429, 1218, 1079 $cm^{-1}$.

Figure 5J:
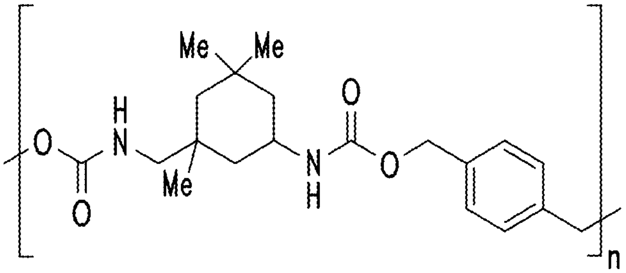

Referring to FIG. 5J, polyurethane PUj was prepared according to general procedure using nBuCPI 1a (1.00 g, 2.14 mmol, 2.00 equiv), isophoronediamine bX6 (cis- and trans-mixture, 182 mg, 1.07 mmol, 1.00 equiv) and p-xylene dibromide bE1 (282 mg, 1.07 mmol, 1.00 equiv) with 24 h reaction time RT. $CH_2Cl_2/CH_3CN$ (1:4, 5.0 mL) was used as solvent instead of only toluene to increase solubility. Precipitation in $CH_3CN$ (150 mL) and rinsing with $CH_3CN$ (20 mL) afforded PUj as a white powder (193 mg, 50%). $^1H$ NMR (500 MHz, $CDCl_3$) δ 7.32 (br s, 4H), 5.06 (br s, 4H), 4.95-4.50 (m, 2H), 4.02-3.50 (m, 2H), 3.00-2.75 (m, 2H), 1.94-1.52 (m, 4H), 1.09-0.68 (m, 11H) ppm; $T_{dec}$=253° C.; $T_g$=109° C.; $M_n$=5.1 kDa, Đ=1.19; IR (ATR) 3334, 2924, 1712, 1511, 1218 $cm^{-1}$.

Figure 5K:
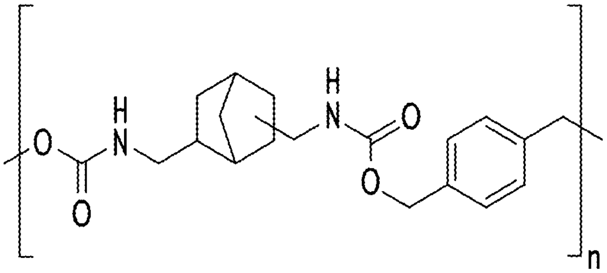

Referring to FIG. 5K, polyurethane PUK was prepared according to general procedure using nBuCPI 1a (1.00 g, 2.14 mmol, 2.00 equiv), bis(aminomethyl) norbornane bX7 (mixture of isomers, 164 mg, 0.534 mmol, 1.00 equiv) and p-xylene dibromide bE1 (282 mg, 0.534 mmol, 1.00 equiv) with 24 h reaction time at RT. $CH_2Cl_2/CH_3CN$ (1:4, 5.0 mL) was used as solvent instead of only toluene to increase solubility. Precipitation in $CH_3CN$ (150 mL) and rinsing with $CH_3CN$ (20 mL) afforded PUK as a white powder (268 mg, 73%). $^1H$ NMR (500 MHz, $CDCl_3$) δ 7.30 (br s, 4H), 5.20-4.30 (m, 4H), 3.83-2.70 (m, 4H), 2.64-0.33 (m, 10H) ppm; $T_{dec}$=240° C.; $T_g$=108° C.; $M_n$=17 kDa, Đ=2.31; IR (ATR) 3329, 2932, 1705, 1515, 1448, 1247, 1134 $cm^{-1}$.

Figure 5L:
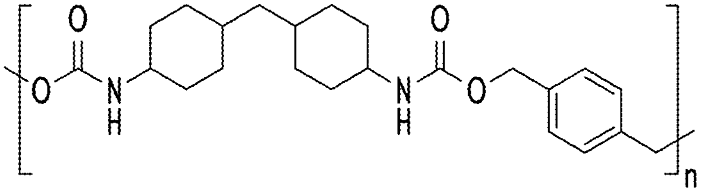

Referring to FIG. 5L, polyurethane PUI was prepared according to general procedure using nBuCPI (1.00 g, 2.14 mmol, 2.00 equiv), 4,4'-methylenebis(cyclohexylamine) bX8 (mixture of isomers, 225 mg, 1.07 mmol, 1.00 equiv) and p-xylene dibromide bE1 (282 mg, 1.07 mmol, 1.00 equiv) with 24 h reaction time at RT. $CH_2Cl_2/CH_3CN$ (1:4, 5.0 mL) was used as solvent instead of only toluene to increase solubility. Precipitation in MeOH (150 mL) and rinsing with MeOH (20 mL) afforded PUK as a white powder (337 mg, 79%). $^1H$ NMR (500 MHz, $CDCl_3$) δ 7.34 (s, 4H), 5.19-4.97 (m, 4H), 4.92-4.51 (m, 2H), 3.84-3.34 (m, 2H), 1.92-0.83 (m, 22H) ppm; $T_{dec}$=242° C.; $T_g$=89.3° C.; $M_n$=4.0 kDa, Đ=1.25; IR (ATR) 3318, 2933, 1683, 1532, 1272, 1225, 1057 $cm^{-1}$.

Figure 5M:
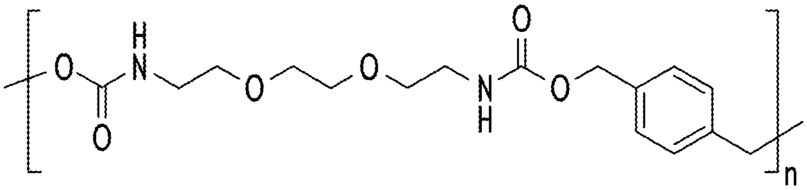

Referring to FIG. 5M, polyurethane PUm was prepared according to general procedure using nBuCPI 1a (500 mg, 1.07 mmol, 2.00 equiv), 1,8-diamino-3,6-dioxaoctane bX9 (79.2 mg, 0.534 mmol, 1.00 equiv) and p-xylene dibromide bE1 (141 mg, 0.534 mmol, 1.00 equiv) with 24 h reaction time at 80° C. Precipitation in toluene/hexanes/1 M $Na_2CO_3$ (1:2:2; 3×250 mL) afforded PUm as a colorless glass (123 mg, 68%). $^1H$ NMR (500 MHz, $CDCl_3$) δ 7.48-7.29 (m, 4H), 5.45 (br s, 2H), 5.07 (s, 4H), 3.70-3.28 (m, 12H) ppm; $T_{dec}$=257° C.; $T_g$=13.5° C.; $M_n$=34.1 kDa, Đ=1.30; IR (ATR) 3327, 2866, 1702, 1515, 1453, 1248, 1102 $cm^{-1}$.

Figure 5N:
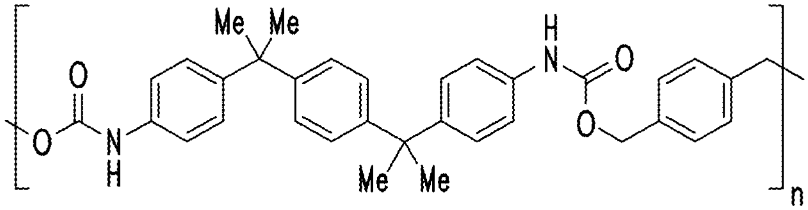

Referring to FIG. 5N, polyurethane PUn was prepared according to general procedure using nBuCPI 1a (500 mg, 1.07 mmol, 2.00 equiv), 4,4'-(1,4-phenylenediisopropylidene)bisaniline bX10 (184 mg, 0.534 mmol, 1.00 equiv) and p-xylene dibromide bE1 (141 mg, 0.534 mmol, 1.00 equiv) with 24 h reaction time at 80° C. Precipitation in MeOH (150 mL) and rinsing with MeOH (20 mL) afforded PUn as a white solid (262 mg, 92%). $^1H$ NMR (400 MHz, $CDCl_3$) δ 7.44-7.29 (m, 4H), 7.16-6.49 (m, 14H), 5.16 (s, 4H), 1.64 (s, 12H) ppm; $T_{dec}$=202° C.; $T_g$=142° C.; $M_n$=6.93 kDa, Đ=1.42; IR (ATR) 3315, 2967, 1713, 1520, 1408, 1318, 1218, 1053 $cm^{-1}$.

Depolymerization From Hydrogenation (H-CRM)

Figure 6A:
FIGS. 6A, 6B, and 6C respectively show depolymerization via hydrogenations of PUa, PUc, and PUf, according to aspects of the invention.
Figure 6B:
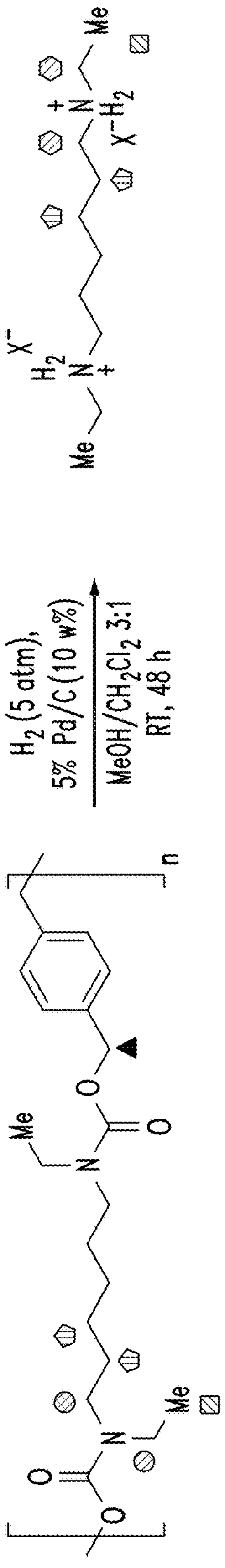
Figure 6C:
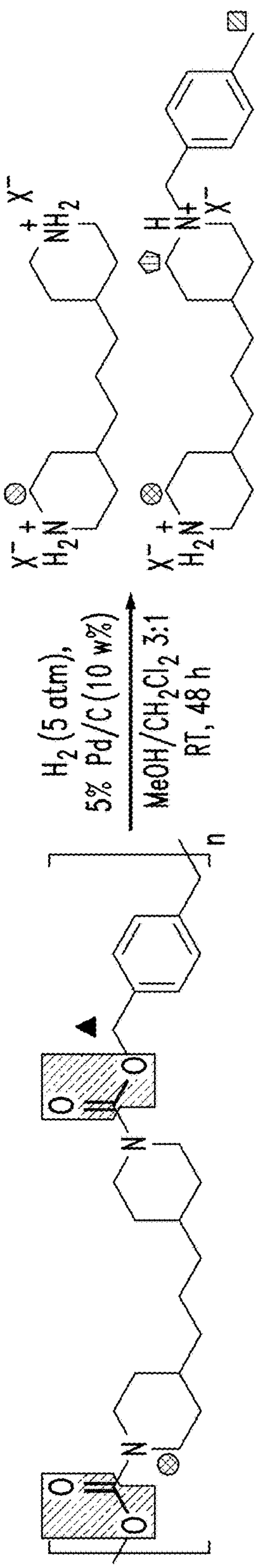

Refer now to FIGS. 6A-6C. FIG. 6A (top) presents a general equation for depolymerization from hydrogenation.

A scintillation vial was charged with a stir bar, polymer, and 5% Pd/C (10%) (5% refers to the weight percentage of catalyst to polymer while 10% refers to the weight percent of palladium to carbon). A 3:1 solution of MeOH:DCM was added to the vial (5 mL/100 mg of polymer). The vial was placed in the hydrogenation reactor and sealed. The hydrogenation reactor was purged with hydrogen ($H_2$) three times. The reactor was pressurized with $H_2$ to 5 atm and placed on a stir plate. The mixture was stirred at room temperature for 48 hours. The resulting solution was taken out of the hydrogenation reactor and filtered through celite with the 3:1 solution of MeOH:DCM. The crude material was concentrated under vacuum and analyzed to determine depolymerization degree and identity of the formed depolymerized species.

FIG. 6A shows depolymerization of PUa. The top of FIG. 6A presents a general equation for depolymerization from hydrogenation. FIG. 6B shows depolymerization of PUc. FIG. 6C shows depolymerization of PUf. In each case, Xylene was not recovered as it evaporated during workup.

Depolymerization From Acid-Catalyzed Bromide Substitution (Br-CRM)

Figure 7A:
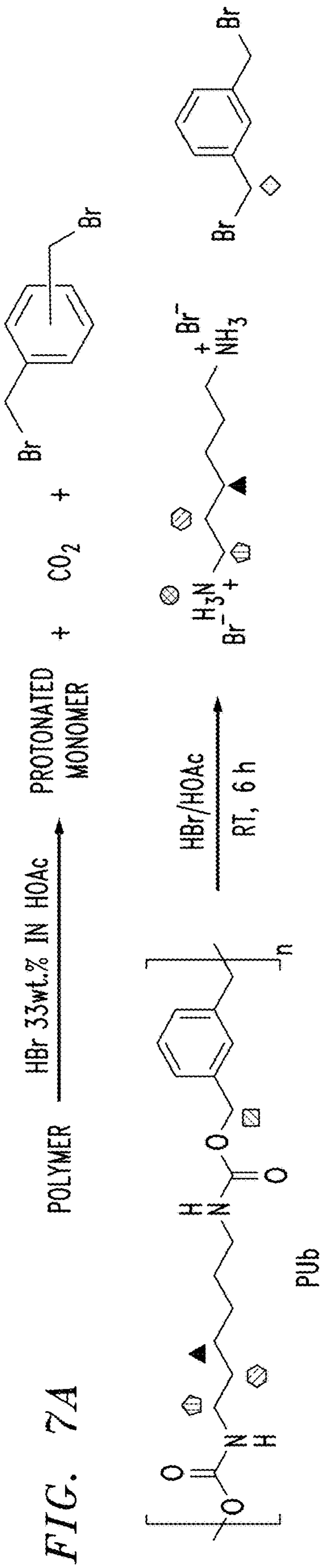
FIGS. 7A, 7B, and 7C respectively show depolymerization via acid-catalyzed Br-substitution of PUb, PUd, and PUf, according to aspects of the invention It is to be appreciated that elements in the figures are illustrated for simplicity and clarity. Common but well-understood elements that may be useful or necessary in a commercially feasible embodiment may not be shown in order to facilitate a less hindered view of the illustrated embodiments.
Figure 7B:
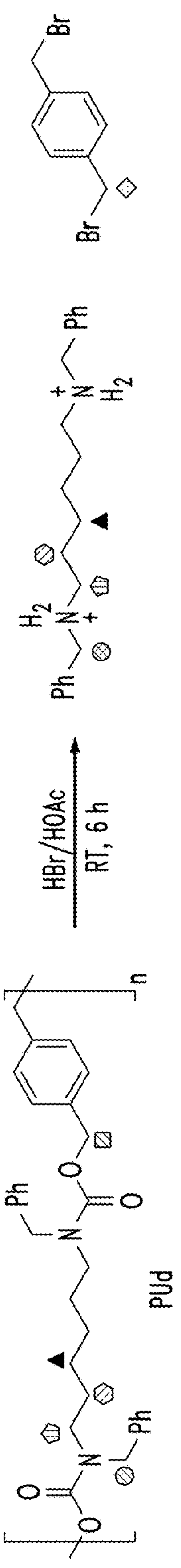
Figure 7C:
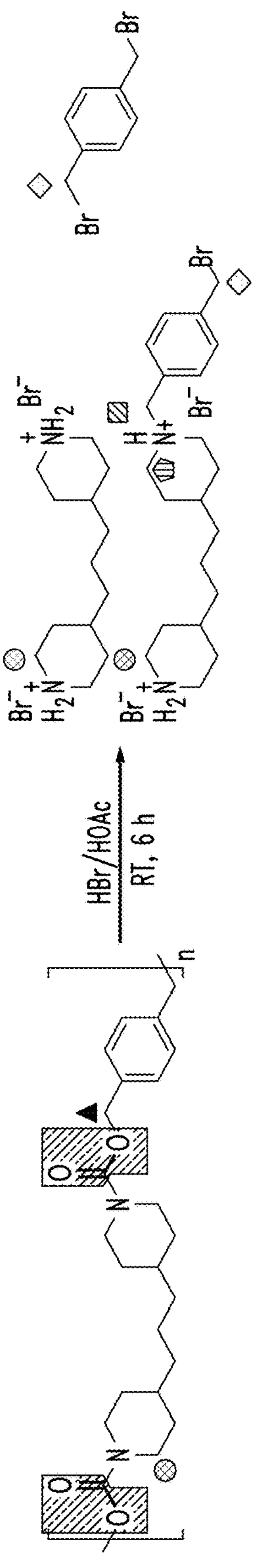

Refer now to FIGS. 7A-7C. FIG. 7A (top) presents a general equation for depolymerization from acid-catalyzed bromide substitution.

A scintillation vial was charged with a stir bar, polymer (100-200 mg) and HBr (1.5 mL, 33 wt. % in acetic acid). Immediate formation of $CO_2$ was observed upon addition of HBr. After stirring for 6 h at RT, the reaction was precipitated in $Et_2O$ and filtered giving the protonated monomer and xylene dibromide in a quantitative manner. After drying in vacuo, the depolymerized residue was submitted for $^1H$ NMR analysis (DMSO-$d_6$) to determine depolymerization degree and identity of the formed depolymerized species.

FIG. 7A bottom shows depolymerization of PUb. FIG. 7B shows depolymerization of PUd. FIG. 7C shows depolymerization of PUf.

Preparation of Small Molecule Carbonates and Carbamates nBuCPI (1 equiv) was suspended in acetonitrile (100 mM) and bubbled with $CO_2$ through balloon and needle. When the cyclopropenimine-$CO_2$ complex was fully dissolved, alcohol/amine (1 equiv) or diamine (0.5 equiv) were added and stirred for 10 min. Benzyl bromide or 1-(bromomethyl)-2-nitrobenzene (1 equiv) were added and treated to appropriate conditions of time and temperature. The solution was evaporated, and the residue was adsorbed on silica and purified via flash column chromatography to give the desired carbonate or carbamate.

Given the discussion thus far, and recalling the example(s) re hydrogenolysis (H-CRM) in the presence of a catalyst, it will be appreciated that, in general terms, an exemplary method for depolymerizing polyurethanes includes introducing into a reactor a polyurethane having a benzylic linkage (e.g., between the carboxy functionalities); and inducing a chemical reduction through a reducing agent and a catalyst to depolymerize the polyurethane having the benzylic linkage.

In one or more embodiments, the reducing agent includes hydrogen. Thus, some embodiments further include introducing hydrogen and a catalyst into the reactor.

In some instances, the chemical reduction includes reacting the polyurethane with the hydrogen in the presence of the catalyst to recover constituents (e.g., constituent monomers) of the polyurethane via hydrogenolysis to cleave the benzylic linkage of the polyurethane.

In one or more embodiments, the catalyst comprises palladium over carbon.

Note in FIG. 2E the benzylic linkage 2999 which advantageously allows depolymerization at room temperature under mild conditions. The polyurethanes having the advantageous benzylic linkage 2999 can be prepared as described herein with reference to FIG. 1B. Referring to FIG. 1B structure 321—polymerization from depicted monomers (bis-electrophiles (bE)) provide the desired linkage.

Generally, the polyurethanes can be, for example, N-alkylated polyurethanes or NH-polyurethanes.

Advantageously, one or more embodiments of the method can be carried out at room temperature.

One or more embodiments can be carried out at one atmosphere. For example, the hydrogen can be maintained at a pressure of one atmosphere and the catalyst can include, for example, a palladium on carbon catalyst.

In one or more embodiments, the recovered constituents include amines 2993 and xylene 2997.

In some cases, the recovered constituents include secondary amines such as bX5a.

Generally, in FIG. 3, any polymer listed with electrophiles bE1 or bE2 can be employed.

Thus, the polyurethane can have the chemical structure PUa, PUb, PUc, PUd, PUe, PUf, PUg, PUj, PUK, PUI, PUm, or PUn. For example, the polyurethane can have the chemical structure shown at the left-hand side of FIG. 2E and R can be selected from the group consisting of hydrogen (PUa), an ethyl group (PUc), and a benzyl group (PUd).

Furthermore, given the discussion thus far, and recalling the example(s) re depolymerization in the presence of HBr, it will be appreciated that, in general terms, another exemplary method for depolymerizing polyurethanes includes introducing into a reactor a polyurethane having a benzylic linkage; introducing hydrogen bromide into the reactor; and reacting the polyurethane with the hydrogen bromide to recover constituents (e.g., constituent monomers) of the polyurethane via acid-catalyzed bromine-substitution to cleave the benzylic linkage of the polyurethane.

Generally, both disclosed depolymerization reactions are possible because polyurethanes contain the structure 2999. In the case of the acid-catalyzed bromine-substitution, structures 2995 are generated and the amines 2991 are regenerated.

One or more embodiments further include introducing acetic acid into the reactor as a solvent.

In one or more embodiments, the recovered constituents include amines 2991 and dibromoxylene 2995.

In some cases, the recovered constituents include secondary amines such as bX5a.

Generally, the polyurethanes can be, for example, N-alkylated polyurethanes or NH-polyurethanes.

Advantageously, one or more embodiments of the HBr method can be carried out at room temperature.

Generally, in FIG. 3, any polymer listed with electrophiles bE1 or bE2 can be employed for the HBr method, as well.

Thus, the polyurethane for the HBr method can have the chemical structure PUa, PUb, PUc, PUd, PUe, PUf, PUg, PUj, PUk, PUI, PUm, or PUn. For example, the polyurethane can have the chemical structure shown at the left-hand side of FIG. 2E and R can be selected from the group consisting of hydrogen (PUa), an ethyl group (PUc), and a benzyl group (PUd).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for depolymerizing polyurethanes, comprising:

introducing into a reactor a polyurethane having a benzylic linkage; and inducing a chemical reduction through a reducing agent and a catalyst to depolymerize the polyurethane having the benzylic linkage.

2. The method of claim 1, wherein the reducing agent comprises hydrogen.

3. The method of claim 2, wherein the chemical reduction comprises reacting the polyurethane with the hydrogen in the presence of the catalyst to recover constituents of the polyurethane via hydrogenolysis to cleave the benzylic linkage of the polyurethane.

4. The method of claim 3, wherein the catalyst comprises palladium over carbon.

5. The method of claim 4, wherein the recovered constituents include amines and xylene.

6. The method of claim 5, wherein the recovered constituents include secondary amines.

7. The method of claim 4, wherein the reacting is carried out at room temperature.

8. The method of claim 7, wherein the reacting is carried out at one atmosphere.

9. The method of claim 1, wherein the polyurethane has a chemical structure:

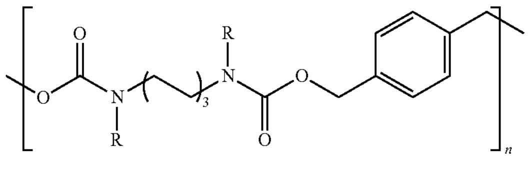

wherein R is selected from the group consisting of hydrogen, an ethyl group, and a benzyl group.

10. The method of claim 1, wherein the polyurethane has a chemical structure:

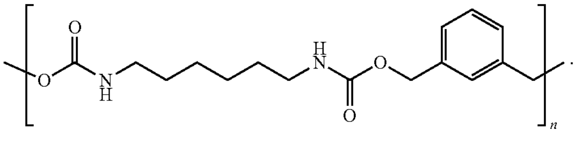

11. The method of claim 1, wherein the polyurethane has a chemical structure:

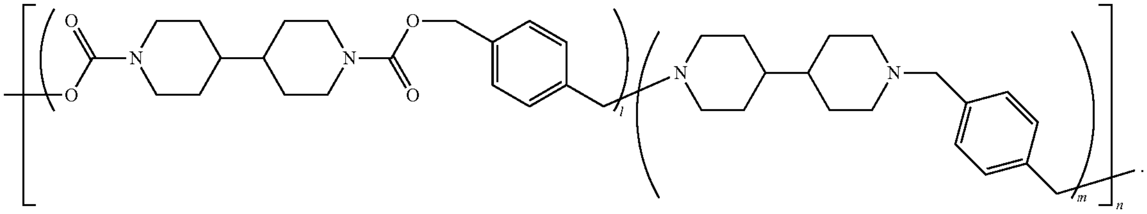

12. The method of claim 1, wherein the polyurethane has a chemical structure:

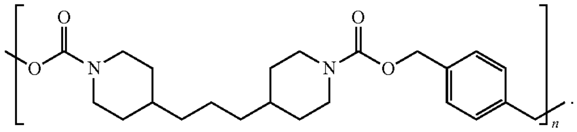

13. The method of claim 1, wherein the polyurethane has a chemical structure:

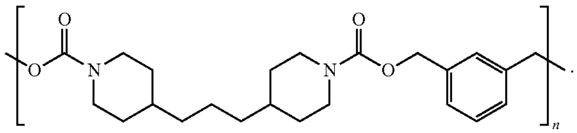

14. The method of claim 1, wherein the polyurethane has a chemical structure:

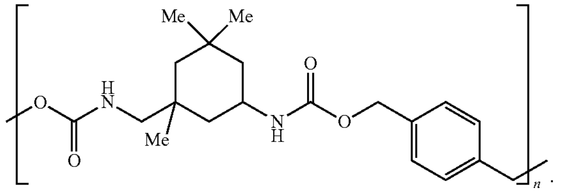

15. The method of claim 1, wherein the polyurethane has a chemical structure:

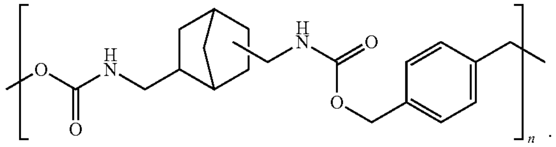

16. The method of claim 1, wherein the polyurethane has a chemical structure:

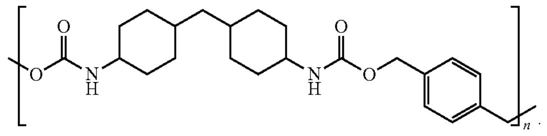

17. The method of claim 1, wherein the polyurethane has a chemical structure:

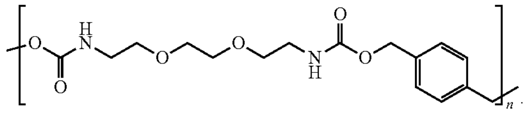

18. The method of claim 1, wherein the polyurethane has a chemical structure:

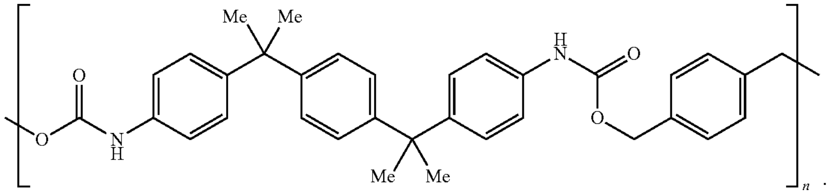

19. A method for depolymerizing polyurethanes, comprising:

introducing into a reactor a polyurethane having a benzylic linkage;

introducing hydrogen bromide into the reactor; and reacting the polyurethane with the hydrogen bromide to recover constituents of the polyurethane via acid-catalyzed bromine-substitution to cleave the benzylic linkage of the polyurethane.

20. The method of claim 19, further comprising introducing acetic acid into the reactor as a solvent.

21. The method of claim 20, wherein the recovered constituents include amines and dibromoxylene.

22. The method of claim 21, wherein the recovered constituents include secondary amines.

23. The method of claim 19, wherein the reacting is carried out at room temperature.

24. The method of claim 23, wherein the reacting is carried out at one atmosphere.

25. The method of claim 19, wherein the polyurethane has a chemical structure:

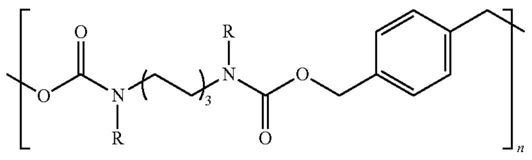

wherein R is selected from the group consisting of hydrogen, an ethyl group, and a benzyl group.

26. The method of claim 19, wherein the polyurethane has a chemical structure:

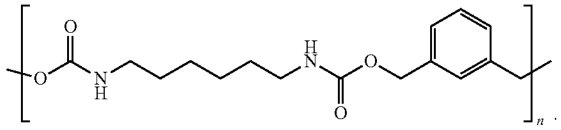

27. The method of claim 19, wherein the polyurethane has a chemical structure:

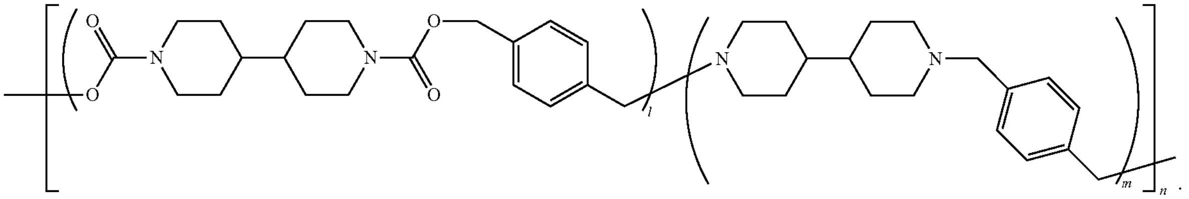

28. The method of claim 19, wherein the polyurethane has a chemical structure:

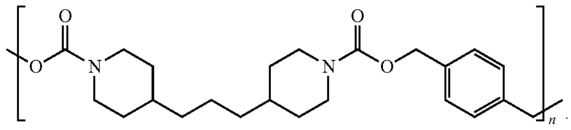

29. The method of claim 19, wherein the polyurethane has a chemical structure:

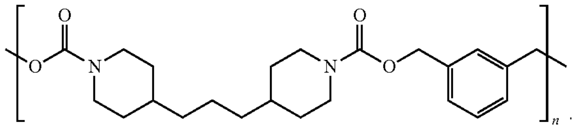

30. The method of claim 19, wherein the polyurethane has a chemical structure:

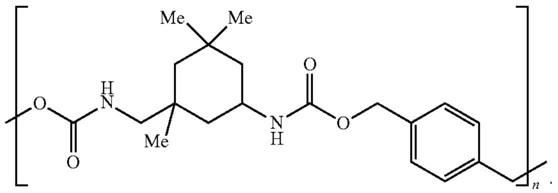

31. The method of claim 19, wherein the polyurethane has a chemical structure:

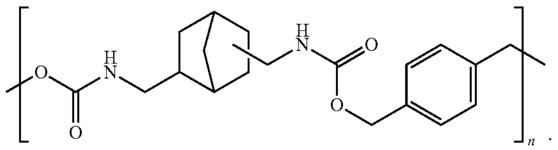

32. The method of claim 19, wherein the polyurethane has a chemical structure:

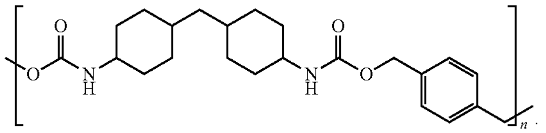

33. The method of claim 19, wherein the polyurethane has a chemical structure:

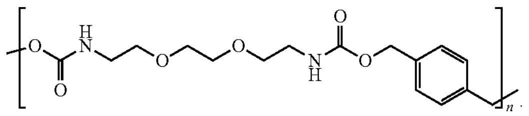

34. The method of claim 19, wherein the polyurethane has a chemical structure:
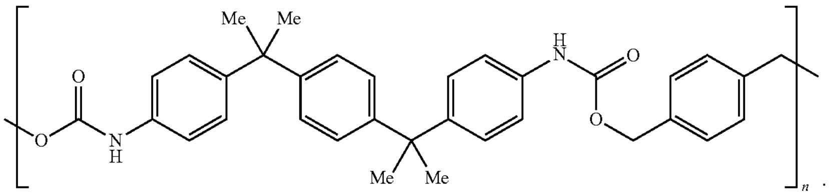
* * * * *